United States Patent
Czech et al.

(10) Patent No.: US 8,685,376 B2
(45) Date of Patent: Apr. 1, 2014

(54) EMULSIFIER INCLUDING GLYCERIN-MODIFIED ORGANOPOLYSILOXANES

(75) Inventors: Karin Czech, Essen (DE); Ulrike Mahring, Essen (DE); Michael Ferenz, Essen (DE); Christian Hartung, Essen (DE); Hannelore Foetsch, Essen (DE); Juergen Meyer, Essen (DE); Sascha Herrwerth, Essen (DE)

(73) Assignee: Evonik Goldschmidt GmbH, Essen (DE)

(*) Notice: Subject to any disclaimer, the term of this patent is extended or adjusted under 35 U.S.C. 154(b) by 311 days.

(21) Appl. No.: 12/761,750

(22) Filed: Apr. 16, 2010

(65) Prior Publication Data
US 2010/0266651 A1 Oct. 21, 2010

(30) Foreign Application Priority Data
Apr. 16, 2009 (DE) .................. 10 2009 002 415

(51) Int. Cl.
*A61Q 19/00* (2006.01)
*A61Q 5/00* (2006.01)
*A61K 8/894* (2006.01)
*C08L 83/12* (2006.01)

(52) U.S. Cl.
USPC ........ 424/70.19; 524/588; 556/450; 556/453; 556/455; 556/456

(58) Field of Classification Search
USPC .................. 556/450, 455, 456, 453; 524/588; 424/70.19
See application file for complete search history.

(56) References Cited

U.S. PATENT DOCUMENTS

| | | | |
|---|---|---|---|
| 3,775,452 A | 11/1973 | Karstedt | |
| 5,144,054 A | 9/1992 | Shioya et al. | |
| 5,262,155 A | 11/1993 | Vincent et al. | |
| 5,976,521 A * | 11/1999 | Briggs et al. | 424/78.07 |
| 7,196,153 B2 | 3/2007 | Burkhart et al. | |
| 7,442,666 B2 | 10/2008 | Herrwerth et al. | |
| 7,598,334 B2 | 10/2009 | Ferenz et al. | |
| 7,605,284 B2 | 10/2009 | Brueckner et al. | |
| 7,635,581 B2 | 12/2009 | Ferenz et al. | |
| 2005/0136269 A1 | 6/2005 | Doehler et al. | |
| 2005/0261133 A1 | 11/2005 | Nakanishi et al. | |
| 2006/0188455 A1 | 8/2006 | Ferenz et al. | |
| 2006/0204468 A1 | 9/2006 | Allef et al. | |
| 2007/0092470 A1 | 4/2007 | Allef et al. | |
| 2007/0128143 A1 | 6/2007 | Gruning et al. | |
| 2007/0178144 A1 | 8/2007 | Hameyer et al. | |
| 2007/0299231 A1 | 12/2007 | Doehler et al. | |
| 2008/0064782 A1 | 3/2008 | Doehler et al. | |
| 2008/0311060 A1 | 12/2008 | Sakuta et al. | |
| 2009/0062459 A1 | 3/2009 | Thum et al. | |
| 2009/0093598 A1 | 4/2009 | Venzmer et al. | |
| 2010/0034765 A1 | 2/2010 | Herrwerth et al. | |
| 2010/0036011 A1 | 2/2010 | De Gans et al. | |
| 2010/0056818 A1 | 3/2010 | Ferenz et al. | |
| 2010/0081763 A1 | 4/2010 | Meyer et al. | |

FOREIGN PATENT DOCUMENTS

| | | |
|---|---|---|
| DE | 102008001788 A1 | 11/2009 |
| EP | 0475130 A2 | 3/1992 |
| EP | 1213316 A2 | 6/2002 |
| EP | 1520870 A1 | 4/2005 |
| EP | 1550687 A1 | 7/2005 |
| EP | 1816154 A1 | 8/2007 |

OTHER PUBLICATIONS

European Search Report dated Jun. 2, 2010.

\* cited by examiner

*Primary Examiner* — Richard Schnizer
*Assistant Examiner* — Alma Pipic
(74) *Attorney, Agent, or Firm* — Scully, Scott, Murphy & Presser, P.C.

(57) ABSTRACT

The invention relates to emulsifiers comprising glycerin-modified organopolysiloxanes and to their use for the preparation of extraordinarily stable emulsions and dispersions.

13 Claims, No Drawings

EMULSIFIER INCLUDING GLYCERIN-MODIFIED ORGANOPOLYSILOXANES

FIELD OF THE INVENTION

The invention relates to emulsifiers comprising glycerin-modified organopolysiloxanes of a specific general formula and to their use for the preparation of extraordinarily stable emulsions and dispersions.

BACKGROUND OF THE INVENTION

Organomodified siloxanes are used in a very wide variety of applications. The properties of organomodified siloxanes can be specifically adjusted by the type of modification employed and also by the modification density.

Thus, for example, with allyl polyethers, organophilic or nonionic hydrophilic groups can be bonded to a siloxane backbone. Compounds of this type are used, for example, as polyurethane foam stabilizers and as antifoams in fuels.

By contrast, through reaction with alpha-olefins, the siloxane is linked to oleophilic groups. The silicone waxes obtained in this way serve, for example, as additives in cosmetic applications.

In many fields of application, it is found that the effect of the siloxane depends decisively on the compatibility with the corresponding formulation. Suitable emulsifiers are, for example, siloxanes which, besides aliphatic groups based on alpha-olefins, carry polyethers, such as, for example, the commercial product ABIL® EM 90 from Evonik Goldschmidt GmbH, Germany.

Since polyether-containing compounds have recently received increasing criticism, there is a need for siloxane-based emulsifiers which carry no polyether groups, but at the same time have good emulsifying and dispersing properties.

For example, glycerin derivatives or polyglycerin derivatives can replace the polyether groups as a hydrophilic component. Polyglycerin-modified siloxanes are described, for example, in EP 1213316. In the application EP 1550687 (Shin-Etsu), glycerin-modified siloxanes are used in emulsions. Polyglycerin-modified siloxanes are also commercially available, for example from Shin-Etsu under the names KF-6100 or KSG-710.

However, the glycerin-modified siloxane compounds described hitherto are generally not suitable for adequately stabilizing emulsions and dispersions—as is necessary, for example, for commercial, and cosmetic formulations. Formulations have to be storage-stable in order to ensure appropriate durability and constant quality of the end product. For this, the emulsions or dispersions have to exhibit a constantly stable composition and homogeneity without oil separation or water separation or solids separation over a period of several months and at various temperatures. Specifically in the case of cosmetic emulsion preparations for make-up and sunscreen applications, which additionally comprise inorganic pigments such as, for example, titanium dioxide or iron oxides, it is often difficult to prepare cosmetic preparations which are characterized by good long-term stability and by a very good pigment dispersion. Here, the glycerin-based silicone emulsifiers described in the prior art generally have inadequate emulsion stabilization. Emulsions which are prepared with the help of the glycerin-containing silicone emulsifiers described in the prior art can separate upon storage and thus lead to inadequate stability and nonreproducible results.

SUMMARY OF THE INVENTION

The present invention provides new types of polyether-free, organomodified siloxanes that can be prepared in a reproducible manner and which can be used as powerful emulsifiers and dispersants. The polyether-free, organomodified siloxanes of the present invention when employed as an emulsifier or a dispersant exhibit a reproducibly excellent stabilization of the formulations.

Specifically, the present invention provides polyether-free, organomodified siloxanes selected from glycerin-modified organopolysiloxanes of general formula (I) which can be employed as very powerful emulsifiers and dispersants and thus constitute a significant improvement compared to the systems described hitherto. Emulsions prepared with the inventive glycerin-modified organopolysiloxanes as well as pigment-containing and particle-containing dispersions containing the inventive glycerin-modified organopolysiloxanes are reproducibly very stable.

More specifically, the invention provides an emulsifier comprising at least one glycerin-modified siloxane of the general formula (I)

$$M_{2+f+2g-a-b}M'_aM''_bD_cD'_dD''_eT_fQ_g \qquad \text{formula (I)}$$

where
$M=(R^1_3SiO_{1/2})$,
$M'=(R^1_2R^2SiO_{1/2})$,
$M''=(R^1_2R^3SiO_{1/2})$,
$D=(R^1_2SiO_{2/2})$,
$D'=(R^1R^2SiO_{2/2})$,
$D''=(R^1R^3SiO_{212})$,
$T=(R^1SiO_{3/2})$ and
$Q=(SiO_{4/2})$, where
$R^1$=independently of one another, identical or different linear or branched, optionally aromatic hydrocarbon radicals having 1 to 16 carbon atoms, which optionally carry OH or ester functions, preferably methyl or phenyl, in particular methyl,
$R^2$=independently of one another, identical or different linear or branched, optionally aromatic hydrocarbon radicals having 1 to 30 carbon atoms, preferably linear alkyl radicals having 8 to 28 carbon atoms, in particular n-dodecyl or n-hexadecyl, or an undecylic acid methyl ester radical and
$R^3$=—$CH_2CH_2CH_2OCH_2CH(OH)CH_2OH$, where
  a=0 to 2, in particular 0 to 1,
  b=0 to 2, in particular 0 to 1,
  c=20 to 300, preferably 30 to 220, in particular 40 to 150,
  d=4 to 130, preferably 5 to 80, in particular 8 to 40,
  e=3 to 75, preferably 3.5 to 45, in particular 4 to 25,
  f=0 to 10, preferably 0 to 5, in particular 0 and
  g=0 to 5, preferably 0 to 2, in particular 0
with the proviso that
  N=2+c+d+e+2f+3g=51 to 350, preferably 60 to 250, in particular 65 to 180,
  y=(a+d)/(b+e)=1 to 6.5, preferably 1.3 to 6, in particular 1.5 to 5.5 and
  z=a+b+d+e=greater than 10, preferably greater than 12, in particular greater than 14.

DETAILED DESCRIPTION OF THE INVENTION

The emulsifiers according to the invention are described below by way of example without any intention to limit the invention to these exemplary embodiments. Where ranges, general formulae or compound classes are given below, these are intended to encompass not only the corresponding ranges or groups of compounds explicitly mentioned, but also all part ranges and part groups of compounds which can be obtained by removing individual values (ranges) or compounds. Where documents are cited within the context of the present description, then their content should be deemed as belonging in its entirety to the disclosure content of the present invention. Where, within the context of the present invention, compounds, such as, for example, organomodified polysiloxanes, are described which can have a plurality of different units, these may occur in random distribution (random oligomer) or occur in an arranged manner (block oligomer) in these compounds. Data relating to the number of units in such compounds is to be understood as meaning the average value, averaged over all of the corresponding compounds.

Within the context of this invention, an emulsifier is to be understood as meaning an emulsifier which comprising, consists essentially of, or consists of at least one substance of the general formula (I) and optionally at least one coemulsifier. In one embodiment, the presence of a coemulsifier is preferred.

The invention provides an emulsifier comprising at least one glycerin-modified siloxane of the general formula (I)

$$M_{2+f+2g-a-b}M'_aM''_bD_cD'_dD''_eT_fQ_g \qquad \text{formula (I)}$$

where
 $M=(R^1{}_3SiO_{1/2})$,
 $M'=(R^1{}_2R^2SiO_{1/2})$,
 $M''=(R^1{}_2R^3SiO_{1/2})$,
 $D=(R^1{}_2SiO_{2/2})$,
 $D'=(R^1R^2SiO_{2/2})$,
 $D''=(R^1R^3SiO_{2/2})$,
 $T=(R^1SiO_{3/2})$ and
 $Q=(SiO_{4/2})$,
where
 $R^1$=independently of one another, identical or different linear or branched, optionally aromatic hydrocarbon radicals having 1 to 16 carbon atoms, which optionally carry OH or ester functions, preferably methyl or phenyl, in particular methyl,
 $R^2$=independently of one another, identical or different linear or branched, optionally aromatic hydrocarbon radicals having 1 to 30 carbon atoms, preferably linear alkyl radicals having 8 to 28 carbon atoms, in particular n-dodecyl or n-hexadecyl, or an undecylic acid methyl ester radical and
 $R^3$=—CH$_2$CH$_2$CH$_2$OCH$_2$CH(OH)CH$_2$OH,
where
 a=0 to 2, in particular 0 to 1,
 b=0 to 2, in particular 0 to 1,
 c=20 to 300, preferably 30 to 220, in particular 40 to 150,
 d=4 to 130, preferably 5 to 80, in particular 8 to 40,
 e=3 to 75, preferably 3.5 to 45, in particular 4 to 25,
 f=0 to 10, preferably 0 to 5, in particular 0 and
 g=0 to 5, preferably 0 to 2, in particular 0
with the proviso that
 N=2+c+d+e+2f+3g=51 to 350, preferably 60 to 250, in particular 65 to 180,
 y=(a+d)/(b+e)=1 to 6.5, preferably 1.3 to 6, in particular 1.5 to 5.5 and
 z=a+b+d+e=greater than 10, preferably greater than 12, in particular greater than 14.
Specifically,
 a) a long silicone backbone N,
 b) with sufficiently high modification density z, and
 c) a selected ratio y of hydrophobic alkyl groups to hydrophilic glycerin groups is critical for a good performance in the formulations.

This interplay provides for very good stabilization of the emulsions described below and has hitherto not been recognized in the prior art.

Preferred emulsifiers according to the invention are characterized in that the glycerin-modified siloxanes present satisfy the proviso that 2≥a+b>0.

For emulsifier according to the invention, it may be advantageous if the glycerin-modified siloxanes present have further branches in order, if appropriate, to result in higher molecular weights and in a broader molecular weight distribution. This can lead to advantages in connection with an emulsion-stabilizing effect.

Consequently, the present invention further provides an emulsifier comprising glycerin-modified siloxanes of the formula (I) with the above-described parameters which additionally comprise siloxane units of the general formula (II).

$$[D'''\text{-}R^4\text{-}D'''] \qquad \text{formula (II)}$$

where
 $D'''(R^1SiO_{2/2})$,
where
 $R^1$ is as defined in formula (I),
 $R^4$=—CH$_2$CHR$^1$—R$^5$—CHR$^1$CH$_2$— or —CH=CR$^1$—R$^5$—CR$^1$=CH— and
 $R^5$=a linear or branched alkylene radical which optionally has ether, alcohol, ester, amine or siloxane groups, or a radical of the general formula —(Si(CH$_3$)$_2$O)$_h$—Si(CH$_3$)$_2$— (where h=1-400), e.g. —(CH$_2$)$_4$—, —(CH$_2$)$_8$—, —CH$_2$OCH$_2$—, —CH$_2$OCH$_2$C(CH$_2$CH$_3$)(CH$_2$OH)CH$_2$OCH$_2$—, —Si(CH$_3$)$_2$O—Si(CH$_3$)$_2$—.

It is evident that mixtures of the glycerin-modified siloxanes may be present in the emulsifier according to the invention. In this regard, it is preferred that the emulsifier according to the invention comprises mixtures of the glycerin-modified siloxanes with different Si chain lengths, defined in formula (I) as N.

The organomodified siloxanes can be prepared by hydrosilylation. The SiH-functional siloxanes used for the hydrosilylation are obtainable by the processes of equilibration, known to a person skilled in the art, as described, for example, in U.S. Pat. No. 7,196,153 B2.

Glycerol monoallyl ether can be obtained, for example, from Raschig. Alpha-olefins such as 1-dodecene or 1-hexadecene are commercially available, for example, from Shell or Chevron Chemical.

The hydrosilylation can be carried out by established methods in the presence of a catalyst. In this regard, it is possible to use, for example, catalysts such as platinum complexes, rhodium complexes, osmium complexes, ruthenium complexes, palladium complexes, iridium complexes or similar compounds or the corresponding pure elements or their derivatives immobilized on silica, aluminium oxide or activated carbon or similar support materials. The hydrosilylation can be carried out in the presence of Pt catalysts such as cis-platinum or Karstedt catalyst [tris(divinyltetramethyldisiloxane)bisplatinum]. The amount of catalyst used can be 10$^{-7}$ to 10$^{-1}$ mol per mole of olefin, preferably 1 to 20 ppm. The hydrosilylation can be carried out at temperatures between 0° C. and 200° C., preferably between 50° C. and 140° C. The reaction can be carried out in suitable solvents such as aliphatic or aromatic hydrocarbons, cyclic oligosiloxanes, alcohols, carbonates or esters. By using a solvent it is possible to avoid incompatibilities arising between the starting materials and thus possibly also in the end product, and the initiation of the reaction from occurring at a delayed time. It is also possible to dispense with the use of a solvent. Suitable processes for the hydrosilylation are described, for example, in the book "Chemie and Technologie der Silicone [Chemistry and technology of silicones]", Verlag Chemie, 1960, page 43, and also in U.S. Pat. No. 3,775,452 and EP 1520870, to which reference is expressly made.

To establish certain formulation properties, emulsifiers according to the invention can, if appropriate, be combined with a coemulsifier. Suitable coemulsifiers are in principle all emulsifiers known to a person skilled in the art.

Particular preference is given to the combination with coemulsifiers such as polyglycerin esters of isostearic acid, oleic acid and/or polyhydroxystearic acid or polyricinoleic acid, such as, for example, polyglyceryl-4 isostearate (e.g. ISOLAN® GI 34 (Evonik Goldschmidt GmbH)), polyglyceryl-4 diisostearate/polyhydroxystearate/sebacate (ISOLAN® GPS (Evonik Goldschmidt GmbH)), polyglyceryl-2 dipolyhydroxystearate or polyglyceryl-3 polyricinoleate or with ethoxylated fatty acid esters of polyhydroxystearic acid such as PEG-30 dipolyhydroxystearate.

Furthermore, preferred coemulsifiers are polysiloxane-polyether copolymers (dimethicone copolyols), such as, for example, PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15 dimethicone, or polysiloxane-alkyl-polyether copolymers or corresponding derivatives, such as, for example, lauryl or cetyl dimethicone copolyols, in particular cetyl PEG/PPG-10/1 dimethicone (ABIL® EM 90 (Evonik Goldschmidt GmbH)).

The invention further provides the use of the emulsifiers according to the invention for the preparation of water-in-oil (W/O) or water-in-silicone emulsions which preferably may also comprise inorganic pigments and/or cosmetic particles.

In particular, the emulsifier according to the invention is used for the preparation of cosmetic, dermatological or pharmaceutical formulations, and also for the preparation of care and cleaning compositions for domestic use or industry, in particular for hard surfaces, leather or textiles, optionally comprising dispersed solids.

In this regard, simple water-in-oil or water-in-silicone emulsions are also to be understood as formulations.

Within the present disclosure more preference is given to the use of the inventive emulsifiers for the preparation of cosmetic emulsions which comprise inorganic pigments (such as, for example, titanium dioxide, iron oxides or zinc oxide) and/or cosmetic particles.

Typical particles used in cosmetics have a particle size of 5-50 µm and are used for achieving an improved skin feel, a matting or for the optical reduction of wrinkles ("soft focus effect"). Typical particle materials are PMMA, PE, nylon-12, silicone particles or silicone elastomers, starch and boron nitride. Within the present invention, the particles used may have either a compact structure or else porous structure depending on the profile of properties.

The water-in-oil and water-in-silicone emulsions, in particular the cosmetic, dermatological or pharmaceutical formulations, and also the care and cleaning compositions for domestic use or industry and the care and cleaning compositions for hard surfaces, leather or textiles, optionally comprising dispersed solids, comprise at least one emulsifier according to the invention and are likewise provided by the invention.

In this regard, preferred cosmetic formulations are pigment-containing, in particular inorganic pigment-containing, cosmetic preparations such as, for example, those which comprise iron oxide pigments, titanium dioxide or zinc oxide particles, and formulations which comprise cosmetic particles.

The formulations according to the invention can comprise, for example, at least one additional component selected from the group of
emollients,
coemulsifiers and surfactants,
thickeners/viscosity regulators/stabilizers,
UV photoprotective filters,
antioxidants,
hydrotropes (or polyols),
solids and fillers,
film formers,
pearlescent additives,
deodorant and antiperspirant active ingredients,
insect repellents,
self-tanning agents,
preservatives,
conditioning agents,
perfumes,
dyes,
cosmetic active ingredients,
care additives,
superfatting agents,
solvents.

Substances which can be used as exemplary representatives of the individual groups are known to a person skilled in the art and can be found, for example, in the German application DE 102008001788.4. This patent application is hereby incorporated by reference and thus forms part of the disclosure.

Since the emulsifier according to the invention attains a powerful performance without having to rely on the polyether structures, preferred formulations according to the invention are characterized in that the formulation is essentially free from polyethers and compounds containing polyethers.

In connection with the present invention, the term "essentially free from polyethers and compounds containing polyethers" describes that compounds used contain only traces, preferably no, alkoxy groups, oligoalkoxy groups or polyalkoxy groups, such as, for example, ethylene oxide or propylene oxide. The concentration of compounds containing polyethers should be less than 0.1% by weight, particularly preferably less than 0.01% by weight, based on the total formulation, preferably below the detection limit of customary analytical methods such as, for example, NMR spectroscopy, GPC or MALDI.

Preference is given to the use of emulsifiers according to the invention for the preparation of cosmetic or pharmaceutical formulations. Such formulations may be, for example, creams, lotions or sprays, such as, for example, care creams, baby creams or sunscreen lotions, ointments, antiperspirants, deodorants or make-up. In particular, the cosmetic formulations may also be formulations such as make-ups or sunscreen products which comprise dispersed solids such as, for example, iron oxide pigments, titanium dioxide or zinc oxide particles.

Formulations according to the invention can therefore be used as a skincare product, face care product, head care product, body care product, intimate care product, foot care product, hair care product, nail care product, tooth care product or mouth care product.

Formulations according to the invention can be used in the form of an emulsion, a suspension, a solution, a cream, an ointment, a paste, a gel, an oil, a powder, an aerosol, a stick, a spray, a cleaning product, a make-up or sunscreen preparation or a facial toner.

The present invention is described by way of example in the examples listed below without any intention to limit the invention and its scope of application to the embodiments specified in the examples.

Examples

General procedure for the preparation of the alkyl/glycerin-modified siloxanes according to formula (I):

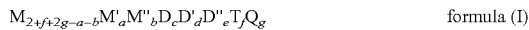

$$M_{2+f+2g-a-b}M'_aM''_bD_cD'_dD''_eT_fQ_g \quad \text{formula (I)}$$

where
M=($R^1_3SiO_{1/2}$),
M'=($R^1_2R^2SiO_{1/2}$),
M''=($R^1_2R^3SiO_{1/2}$),
D=($R^1_2SiO_{2/2}$),
D'=($R^1R^2SiO_{2/2}$),
D'' ($R^1R^3SiO_{2/2}$),
T=($R^1SiO_{3/2}$) and
Q=($SiO_{4/2}$),
where, for the present examples:
$R^1$=methyl,
$R^2$=alkyl or 11-methoxy-11-oxoundecyl,
$R^3$=—$CH_2CH_2CH_2OCH_2CH(OH)CH_2OH$ and
f=g=0.

In a four-neck flask, provided with stirrer, dropping funnel, thermometer and reflux condenser, 1.3·(a+d) mol of alpha-olefin, 1.3·(b+e) mol of glycerin monoallyl ether and 10 ppm of Karstedt catalyst (based on the raw materials without solvent) in ca. 30% toluene (based on the total initial weight) were initially introduced and heated to 95° C. 1 mol of the SiH-siloxane of the general formula (III)

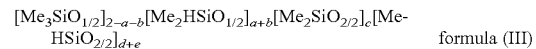

$$[Me_3SiO_{1/2}]_{2-a-b}[Me_2HSiO_{1/2}]_{a+b}[Me_2SiO_{2/2}]_c[MeHSiO_{2/2}]_{d+e} \quad \text{formula (III)}$$

was added dropwise and the mixture was stirred at 95° C. for 2 h. According to SiH value determination, complete conversion of the SiH-siloxane was obtained. Volatile fractions were then distilled off in vacuo at ca. 1 mbar and 110° C. In each case, a viscous, slightly cloudy, almost colorless product was obtained.

Table 1 lists the siloxanes prepared by this general procedure.

TABLE 1

Prepared alkyl/glycerin-modified silicone products according to formula I ($R^1$ = methyl, f = g = 0).

| Siloxane No. | $R^2$ | a + b | N* | a + d | b + e | z* | y* | Emulsion test (comments)* |
|---|---|---|---|---|---|---|---|---|
| Part A |||||||||
| 1 | n-$C_{12}H_{25}$ | 0 | 100 | 22.5 | 2.5 | 25 | 9.0 | --- |
| 2 | n-$C_{12}H_{25}$ | 0 | 100 | 21.8 | 3.2 | 25 | 6.8 | -- |
| 3 | n-$C_{12}H_{25}$ | 0 | 100 | 21 | 4 | 25 | 5.3 | ++ |
| 4 | n-$C_{12}H_{25}$ | 0 | 100 | 18 | 7 | 25 | 2.6 | +++ |
| 5 | n-$C_{12}H_{25}$ | 0 | 100 | 15 | 10 | 25 | 1.5 | ++ |
| 6 | n-$C_{12}H_{25}$ | 0 | 100 | 13 | 12 | 25 | 1.1 | ○ |
| 7 | n-$C_{12}H_{25}$ | 0 | 100 | ≤12 | ≥13 | 25 | ≤0.9 | (siloxanes undergo gelling during preparation) |
| 8 | n-$C_{16}H_{33}$ | 0 | 100 | 18 | 7 | 25 | 2.6 | + |
| 9 | —$(CH_2)_{10}COOCH_3$ | 0 | 100 | 17 | 8 | 25 | 2.1 | ++ |
| 10 | n-$C_{12}H_{25}$ | 0.7 | 150 | 18 | 9 | 27 | 2.0 | ++ |
| Part B |||||||||
| 11 | n-$C_{12}H_{25}$ | 1 | 80 | 12 | 8 | 20 | 1.5 | + |
| 12 | n-$C_{12}H_{25}$ | 0 | 67 | 13 | 7 | 20 | 1.9 | ++ |
| 13 | n-$C_{12}H_{25}$ | 0 | 82 | 9.8 | 5.2 | 15 | 1.9 | ++ |
| 14 | n-$C_{12}H_{25}$ | 0 | 90 | 7 | 3 | 10 | 2.3 | ○ |
| 15 | n-$C_{12}H_{25}$ | 0 | 90 | 5.5 | 4.5 | 10 | 1.2 | ○ |
| 16 | n-$C_{12}H_{25}$ | 0 | 83 | 3.6 | 1.9 | 5.5 | 1.9 | -- |
| Part C |||||||||
| 11 | n-$C_{12}H_{25}$ | 1 | 80 | 12 | 8 | 20 | 1.5 | + |
| 12 | n-$C_{12}H_{25}$ | 0 | 67 | 13 | 7 | 20 | 1.9 | ++ |
| 17 | n-$C_{12}H_{25}$ | 0 | 50 | 13 | 7 | 20 | 1.9 | --- |
| 18 | n-$C_{12}H_{25}$ | 0 | 40 | 13.1 | 6.9 | 20 | 1.9 | --- |
| 19 | n-$C_{10}H_{21}$ | 0 | 19 | 8 | 4 | 12 | 2 | --- |

*N = 2 + c + d + e; z = (a + d) + (b + e); y = (a + d)/(b + e);
+ = good emulsifying power, − = poor emulsifying power.

Moreover, the last column in Table 1 summarizes the emulsifying power of the products in a very critical cosmetic formulation, which permits a rapid differentiation of the emulsion stabilization after just 20 hours. This critical emulsion test is based on the following formulation:

| | | |
|---|---|---|
| A | Alkyl/glycerin-modified silicone emulsifier systems (from Tab. 1) | 1.2% |
| | Ethylhexyl Palmitate | 11.9% |
| | Caprylic/Capric Triglyceride | 11.9% |
| B | Sodium Chloride | 0.8% |
| | Glycerol | 3.0% |
| | Water (demineralized) | 65.2% |
| C | Phenonip ® XB (Clariant) (Phenoxyethanol; Methylparaben; Propylparaben; Ethylparaben) | 1.0% |
| D | Ethanol | 5.0% |

Preparation: Slow addition of Phase B to A with stirring at room temperature; homogenize briefly; addition of Phase C and D; homogenize.

The critical test emulsions were stored for 20 h at 60° C., 50° C. and room temperature. The viscosities of the emulsions after preparation and after storage at 50° C. for 20 h were measured. Furthermore, the emulsions were frozen overnight at −15° C. and then thawed again and assessed. Excellent (+++) emulsion stability refers to an emulsion which in this test exhibited no sign of water or oil separation at all storage temperatures and which, moreover, had no drop in viscosity. Very good (++) emulsion stability indicates at most a trace of water separation upon storage at 60° C. Good (+) emulsion stability may indicate weaknesses in the freezing stability. Ordinary (o) emulsion stability may indicate a more marked water separation at 60° C., and also traces of water separation at 50° C. and indicate weaknesses in the freezing stability. A weak (−) emulsion stability indicates significant signs of water separation at all storage temperatures. A very weak (−−) emulsion stability describes relatively severe water separations at all storage temperatures or clear viscosity drop of the test emulsion coupled with significant water separation at room temperature. A catastrophic (−−−) emulsion stability means that either no W/O emulsion is formed at all or that it separates directly after preparation.

Consequently, the following results arose for the alkyl/glycerin-modified polysiloxanes from Table 1:

Examples 1-7 show that at a constant silicone chain length, which is chosen here to be high (N=100), and also a constant degree of modification, which is likewise chosen to be high (z=25), the ratio y of hydrophobic alkyl groups to hydrophilic glycerin groups has a decisive influence on the emulsion stability. At high glycerin fractions (Example 7), the synthesis leads to unusable products since, on account of the high number of hydroxyl groups, the products can crosslink via SiOC formation and thus in most cases form gels. Good emulsion stability is observed when y=ca. 1.5 to 5.5 (Examples 3-5). Below (Example 6) or above (Examples 1-2) these values, the hydrophilic-to-hydrophobic ratio becomes unfavourable for adequate stabilization. It is necessary for both sufficiently hydrophilic glycerin groups and also a sufficient number of hydrophobic alkyl groups to be present for good emulsion stabilization. Examples 8 and 9 (hexadecyl or undecylic acid methyl ester groups) and Example 10 (additional alpha,omega-modification) have similar parameters to Examples 3-5 and accordingly likewise exhibit good emulsion stabilization.

In Examples 11-16, the silicone chain length is now almost constant and has been chosen to be high (N=67-90), and the ratio of hydrophobic alkyl groups to hydrophilic glycerin groups has been adjusted almost constantly to a good value (y=1.5-2.3) ascertained from the first examples. The parameter of degree of modification z varied here must be >10 to give good results in the emulsion stabilization.

Finally, in Part C of Table 1, the ratio of hydrophobic alkyl groups to hydrophilic glycerin groups (y=1.5-1.9) and the degree of modification (z=20) was kept almost constant at good values and the silicone chain length was varied. It can be seen clearly that a silicone chain length of N>50 is required for good emulsion stabilization.

In summary, it has been established that an alkyl/glycerin-modified siloxane emulsifier with
  a) a long silicone backbone (N>50),
  b) sufficiently high modification density (z>10) and
  c) a selected ratio of hydrophobic alkyl groups to hydrophilic glycerin groups (at least y=1-6.5)
is necessary for a good emulsifying performance in the formulations.

Application Examples

The described cosmetic emulsions are intended to serve to illustrate, by way of example, the ability of the alkyl/glycerin-modified organopolysiloxanes to be used as emulsifiers for cosmetic emulsions.

The preparation was carried out in each case by introducing the water phase into the oil phase and subsequently homogenizing by customary methods.

INCI Nomenclature:

W/O Cream:

|  | 1 | 2 | 3 |
|---|---|---|---|
| Polysiloxane Ex. 4 | 2.0% | | |
| Polysiloxane Ex. 10 | | 2.0% | |
| Polysiloxane Ex. 12 | | | 2.0% |
| Hydrogenated Castor Oil | 0.1% | 0.1% | 0.1% |
| Microcrystalline Wax | 0.1% | 0.1% | 0.1% |
| Isopropyl Palmitate | 8.2% | 8.2% | 8.2% |
| Ethylhexyl Palmitate | 9.6% | 9.6% | 9.6% |
| Sodium Chloride | 0.8% | 0.8% | 0.8% |
| Glycerin | 3.0% | 3.0% | 3.0% |
| Water | ad 100% | ad 100% | ad 100% |
| 2-Bromo-2-nitropropane-1,3-diol | 0.05% | 0.05% | 0.05% |

W/Si Lotion:

|  | 4 | 5 | 6 |
|---|---|---|---|
| Polysiloxane Ex. 4 | 2.0% | | |
| Polysiloxane Ex. 10 | | 2.0% | |
| Polysiloxane Ex. 12 | | | 2.0% |
| Cyclopentasiloxane | 20.8% | 20.8% | 20.8% |
| Sodium Chloride | 0.5% | 0.5% | 0.5% |
| Glycerin | 3.0% | 3.0% | 3.0% |
| Water | ad 100% | ad 100% | ad 100% |
| 2-Bromo-2-nitropropane-1,3-diol | 0.05% | 0.05% | 0.05% |

W/O Body Lotion:

|  | 7 | 8 | 9 |
|---|---|---|---|
| Polysiloxane Ex. 4 | 3.0% | | |
| Polysiloxane Ex. 10 | | 3.0% | 1.0% |
| Polysiloxane Ex. 12 | | | 2.0% |
| Hydrogenated Castor Oil | 0.25% | 0.25% | 0.25% |
| Microcrystatline Wax | 0.25% | 0.25% | 0.25% |
| Ethylhexyl Palmitate | 8.5% | 8.5% | 8.5% |
| Caprylic/Capric Triglyceride | 8.0% | 8.0% | 8.0% |
| Isopropyl Palmitate | 8.0% | 8.0% | 8.0% |
| Sodium Chloride | 0.8% | 0.8% | 0.8% |
| Glycerin | 3.0% | 3.0% | 3.0% |
| Water | ad 100% | ad 100% | ad 100% |
| Phenonip ® XB (Clariant) (Phenoxyethanol; Methylparaben; Propylparaben; Ethylparaben) | 0.7% | 0.7% | 0.7% |

W/O Foundation (Make-Up):

|  | 10 | 11 | 12 | 13 | 14 |
|---|---|---|---|---|---|
| Polysiloxane Ex. 4 | 3.0% | 2.0% | 2.0% | 2.0% | 2.0% |
| Polyglyceryl-4 Diiso-stearate/Polyhydroxystearate/Sebacate [1] |  | 1.0% |  |  |  |
| PEG-30 Dipolyhydroxystearate [2] |  |  | 1.0% |  |  |
| Cetyl PEG/PPG-10/1 Dimethicone [3] |  |  |  | 1.0% |  |
| Bis-PEG/PPG-14/14 Dimethicone; Cyclopentasiloxane [4] |  |  |  |  | 1.0% |
| Diethylhexyl Carbonate | 9.8% | 9.8% | 9.8% | 9.8% | 9.8% |
| Isohexadecane | 6.7% | 6.7% | 6.7% | 6.7% | 6.7% |
| Dimethicone | 1.5% | 1.5% | 1.5% | 1.5% | 1.5% |
| Titanium Dioxide, Alumina, Triethoxycaprylylsilane [5] | 8.0% | 8.0% | 8.0% | 8.0% | 8.0% |
| Iron Oxide [6] | 1.8% | 1.8% | 1.8% | 1.8% | 1.8% |
| Disteardimonium Hectorite | 0.2% | 0.2% | 0.2% | 0.2% | 0.2% |
| Aluminum Starch Octenyl Succinate | 1.5% | 1.5% | 1.5% | 1.5% | 1.5% |
| Nylon-12 | 1.5% | 1.5% | 1.5% | 1.5% | 1.5% |
| Glycerin | 2.0% | 2.0% | 2.0% | 2.0% | 2.0% |
| Sodium Chloride | 0.8% | 0.8% | 0.8% | 0.8% | 0.8% |
| Water | ad 100% | ad 100% | ad 100% | ad 100% | ad 100% |
| Phenonip ® XB (Clariant) (Phenoxyethanol; Methylparaben; Propylparaben; Ethylparaben) | 0.8% | 0.8% | 0.8% | 0.8% | 0.8% |

[1] ISOLAN ® GPS (Evonik Goldschmidt GmbH)
[2] ARLACEL ® P-135 (Croda)
[3] ABIL ® EM 90 (Evonik Goldschmidt GmbH)
[4] ABIL ® EM 97 (Evonik Goldschmidt GmbH)
[5] AC 360 (Kemira)
[6] SICOVIT ® Brown 70E172 (BASF)

In regard to the use of alkyl/glycerin-modified polysiloxanes according to the invention analogous to example formulation 10 it is to be said that these mostly lead to better stabilities and higher color intensities than the customary emulsifiers from the prior art (e.g. ISOLAN® GPS, ARLACEL® P-135, ABIL® EM 90, ABIL® EM 97).

Nevertheless, in individual cases, possibly for reasons of viscosity regulation or for establishing a specific skin feel, a combination with emulsifiers from the prior art may be advantageous. Usually, this is readily possible (example formulations 11-14).

The use of a combination of two emulsifiers according to the invention with different silicone chain lengths may also be particularly advantageous for the emulsion stabilization (example formulation 9).

Besides the use of coated titanium dioxides (e.g. AC 360), the polysiloxane emulsifiers according to the invention are also able to stabilize noncoated pigments. Here too, as a rule higher stability and higher color intensities are obtained than for emulsifiers from the prior art.

W/O—Antiperspirant Roll-On:

|  | 15 | 16 | 17 |
|---|---|---|---|
| Polysiloxane Ex. 4 | 3.0% |  | 2.0% |
| Polysiloxane Ex. 8 |  | 3.0% |  |
| Bis-PEG/PPG-14/14 Dimethicone; Cyclopentasiloxane [4] |  |  | 1.0% |
| Cyclopentasiloxane | 20.0% | 20.0% | 20.0% |
| C12-15 Alkyl Benzoate | 4.0% | 4.0% | 4.0% |
| Silica Silylate [7] | 0.2% | 0.2% | 0.2% |
| Aluminium Chlorhydrate | 20.0% | 20.0% | 20.0% |
| Water | ad 100% | ad 100% | ad 100% |

[4] ABIL ® EM 97 (Evonik Goldschmidt GmbH)
[7] AEROSIL ® R 812 (Evonik Degussa)

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An emulsifier comprising at least one glycerin-modified siloxane of general formula (I)

$$-M_{2+f+2g-a-b}M'_a M''_b D_c D'_d D''_e T_f Q_g \qquad \text{formula (I)}$$

wherein
$M=(R^1_3 SiO_{1/2})$,
$M'=(R^1_2 R^2 SiO_{1/2})$,
$M''=(R^1_2 R^3 SiO_{1/2})$,
$D=(R^1_2 SiO_{2/2})$,
$D'=(R^1 R^2 SiO_{2/2})$,
$D''=(R^1 R^3 SiO_{2/2})$,
$T=(R^1 SiO_{3/2})$ and
$Q=(SiO_{4/2})$,
where
$R^1$=independently of one another, identical or different, methyl or phenyl,
$R^2$=independently of one another, identical or different, linear or branched, optionally aromatic hydrocarbon radicals having 8 to 28 carbon atoms or an undecylic acid methyl ester radical, and
$R^3=-CH_2CH_2CH_2OCH_2CH(OH)CH_2OH$,
where
$a=0$ to 2,
$b=0$ to 2,
$c=20$ to 300,
$d=4$ to 130,
$e=3$ to 75,
$f=0$ to 10 and g=0 to 5 with the proviso that $N=2+c+d+e+2f+3g=51$ to $350$, $y=(a+d)/(b+e)=1.5$ to $5.5$ and $z=a+b+d+e=$ greater than 14.

2. The emulsifier according to claim 1, wherein $2 > a+b > 0$.

3. An emulsifier comprising at least one glycerin-modified siloxane of general formula (I)

$$—M_{2+f+2g-a-b}M'_aM''_bD_cD'_dD''_eT_fQ_g \qquad \text{formula (I)}$$

wherein:

$M=(R^1{}_3SiO_{1/2})$,
$M'=(R^1{}_2R^2SiO_{1/2})$,
$M''=(R^1{}_2R^3Si^O{}_{1/2})$,
$D=(R^1{}_2SiO_{2/2})$,
$D'=(R^1R^2SiO_{2/2})$,
$D''=(R^1R^3SiO_{2/2})$,
$T=(R^1SiO_{3/2})$ and
$Q=(SiO_{4/2})$, where $R^1=$ independently of one another, identical or different, methyl or phenyl, $R^2=$ independently of one another, identical or different, linear or branched, optionally aromatic hydrocarbon radicals having 8 to 28 carbon atoms or an undecylic acid methyl ester radical, and $R^3=$—$CH_2CH_2CH_2OCH_2CH(OH)CH_2OH$, where a=0 to 2, b=0 to 2, c=20 to 300, d=4 to 130, e=3 to 75, f=0 to 10 and g=0 to 5 with the proviso that $N=2+c+d+e+2f+3g=51$ to $350$, $y=(a+d)/(b+e)=1$ to $6.5$ and $z=a+b+d+e=$greater than 10, and wherein the at least one glycerin-modified siloxanes of formula (I) further comprises siloxane units of general formula (II)

$$[D'''-R^4-D'''] \qquad \text{formula (II)}$$

wherein $D'''=(R^1SiO_{2/2})$, where $R^4=$—$CH_2CHR^1$—$R^5$—$CHR^1CH_2$— or —$CH=CR^1$—$R^5$—$CR^1=CH$— and $R^5=$a linear or branched alkylene radical which optionally has ether, alcohol, ester, amine or siloxane groups, or a radical of the general formula —$(Si(CH_3)_2O)_h$—$Si(CH_3)_2$— where h=1-400.

4. The emulsifier according to claim 1, wherein the at least one glycerin-modified siloxane includes a mixture of glycerin-modified siloxanes of formula (I) with different siloxane chain lengths.

5. A method of making a composition comprising providing at least one emulsifier according to claim 1 and adding at least one other ingredient to said at least one emulsifier.

6. The method of claim 5 wherein the at least one other ingredient includes an inorganic pigment or a cosmetic particle.

7. The method of claim 5 wherein the at least one other ingredient is a dispersed solid.

8. A water-in-oil or water-in-silicone emulsion or dispersion comprising at least one emulsifier according to claim 1.

9. A cosmetic, dermatological or pharmaceutical formulation comprising at least one emulsifier according to claim 1.

10. The formulation according to claim 9, wherein the formulation is essentially free from polyethers and compounds containing polyethers.

11. The formulation according to claim 9, further comprising a pigment.

12. A care and cleaning composition comprising at least one emulsifier according to claim 1.

13. The emulsifier according to claim 1, wherein $R^1$ is methyl, $R^2$ is $n-C_{12}H_{25}$, f=0, g=0, a+b=0, N=100, a+d=18, b+e=7, z=25 and y=2.6.

* * * * *